United States Patent [19]

Villa et al.

[11] Patent Number: 5,185,436
[45] Date of Patent: Feb. 9, 1993

[54] ESTERS OF NORMAL BUTYRIC ACID AND THEIR USE AS PHARMACEUTICALS

[75] Inventors: Pierre J. Villa; François Pieri; Ginolino Ronco; Emile P. R. Segard, all of Amiens, France

[73] Assignee: Association Pour La Recherche Therapeutique Anti-Cancereuse, Paris, France

[21] Appl. No.: 501,080

[22] Filed: Mar. 29, 1990

[51] Int. Cl.$^5$ .................. C07H 13/02; C07H 15/04; A61K 31/70
[52] U.S. Cl. ..................... 536/4.1; 536/115; 536/119; 536/120; 514/25
[58] Field of Search ............. 536/4.1, 115, 119, 120; 514/25

[56] References Cited

U.S. PATENT DOCUMENTS 4,497,649 2/1985 Loh ...................... 536/4.1

FOREIGN PATENT DOCUMENTS 55-69596 5/1980 Japan .................... 536/4.1
55-154992 12/1980 Japan .................... 536/4.1

OTHER PUBLICATIONS

J. Chem. Soc (C), issued 1966, Jill Gigg & Roy Gigg, "The Allyl Ethers as a Protecting Group in Carbohydrate Chemistry", see p. 82.

*Primary Examiner*—John W. Rollins
*Assistant Examiner*—Everett White
*Attorney, Agent, or Firm*—Browdy and Neimark

[57] ABSTRACT

Compounds which are hydrolyzed in vivo to n-butyric acid are esters of butyric acid in which the alcohol group is selected from the group consisting of polyhydric alcohols, cyclic and acyclic aldose or ketose monosaccharides and their acetonides. Of particular interest are O-butanoyl-6-O-ispropylidene-1,2,α O-glucofuranose, tri-O-butanoyl 3, 5, 6,- isopropylidene-1,2 α-D-glucofuranose, O-butanoyl-6-di-O-isopropylidene-1,2 : 3,4 α-D-galactopyranose, and penta-O-butanoyl-1,2,3,4,6 D-galactopyranose and penta-O-butanoyl-1,2,3,4,6α D-galactopyranose, )-n-butanoyl-1-isopropylidene-2,3 glyceryl, O-butanoyl-3-di-o-palmitoyl-1,2 glyceryl, and di-O-n butanoyl-2,3 O-palmitoyl-1 glyceryl.

4 Claims, No Drawings

ESTERS OF NORMAL BUTYRIC ACID AND THEIR USE AS PHARMACEUTICALS

BACKGROUND OF THE INVENTION

The present invention relates to n-butyric acid derivatives and their use as a drug.

It is known that the n-butyric acid salts, and most particularly sodium butyrate, possess interesting inhibiting actions on the growth of fibroblasts following actions on the histones and on the structure of the cellular nuclei chromatin. This inhibiting action of the cellular division has proved particularly important to explore in oncology, notably for the treatment of various leukemias, or various sarcomas or carcinomas. In addition to these antimitotic actions at the level of the cellular nuclei, antiviral actions of sodium butyrate have also been characterized for the herpes virus. However, it is also known following pharmacokinetic tests that the mineral salts of n-butyric acid have a lifetime in vivo which is extremely short. In attempts for increasing the half-life of the injected product, other derivatives have also been proposed, as for example the arginine butyrate (Ch. CHANY et al, Int. J. Cancer, 1982, 30, 489; ibid. 1983, 32, 379 and Patent Application EP-A1-0 069 659 (INSERM)). These ionic derivatives do not provide a sufficient in vivo half lifetime for a satisfactory pharmacologic action since they are very quickly eliminated after administration by the intravenous route.

Thus, if sodium n-butyrate is injected at time $t=0$ by the i.v. route and at the rate of 0.12 g per kilogramme of rabbit, the dosages of the n-butyric acid present in mmol per liter of serum are at time $t=2$ min: 1.66 mmol/l; 5 min: 0.87 mmol/l; 18 min: 0.03 mmol/l; 30 min: 0.02 mmol/l.

Under the same conditions, arginine n-butyrate gives the following results: 2 min: 1.36 mmol/l; 5 min: 0.23 mmol/l; 30 min: 0.06 mmol/l; 60 min: 0 mmol/l.

These pharmacokinetic results show that the half life of these compounds in the rabbit blood stream is very short and less than 5 min.

Starting from conclusions admitted at present from the studies made, it is admitted that, for the hereabove saline n-butyrates, the product which is biologically active is the n-butyric acid.

OBJECT OF THE INVENTION

The Applicant has set as an object to synthesize the chemical compounds containing in their structure at least a butanoyl radical bound by a covalent bond to an atoxic carrier compound so that these in vivo compounds, under the action of enzymatic systems in man or animal, slowly release n-butyric acid with as a reult a longer half-life than that of the hereabove saline derivatives and affording therefore a better biodisponibility of the biologically active product.

This aim is reached with the compounds according to the invention and having as formula:

wherein W is a radical of a product having at least one OH group esterifiable by n-butyric acid, whereby n can vary from 1 to the total number of OH groups esterifiable in said product.

Within the scope of the present invention, the product having a radical W plays the role of a temporary transporter for the n-butyric acid and it is particularly advantageous to chose it from amongst less possible toxic products as regards living bodies, insofar as this product is released in system and therefore must be eliminated or metabolized.

In a preferred manner, the ester(s) compounds of the present invention will have a radical W which is part of products chosen from amongst carbohydrates and their acetonide derivatives, hydrogenated carbohydrates and their acetonide derivatives, glyceryl esters of fat acids, acetonide derivative of glycerol, serine and homoserine.

These preferred W radicals are metabolized into compounds which are assimilable by the system with possibly the in situ formation of acetone, which is a compound having little toxicity (median lethal dose p.o. = 10.7 ml/kg of rat—Merck Index 10th edition).

The compounds derivated from aldose or ketose monosaccharides, cyclic or acyclic, and their acetonides, are still more preferred since the in vivo hydrolysis releases, with possibly acetone, butyric acid and a monosaccharide which is a usual nutrient element of man or the animal, therefore atoxic.

The compounds according to the present invention are provided for being used either as drug alone or in association with other compounds used for example, as the n-butyric acid and its salts, for an antitumoral and/or antiviral utilization.

In addition to the hereabove dispositions, the invention includes also other dispositions which will become more apparent from the following description. It is however obvious that this description and the examples it contains are given only by way of illustration of the object of the invention and are in no way limiting.

EXAMPLE 1

Preparation of O-butanoyl-3-di-O-isopropylidene 1,2: 5,6 α-D-glucofuranose (I).

In a three-necked flask are put 26 g (0.1 mole) of di-O-isopropylidene-1,2:5,6 α-D-glucofuranose prepared by methods which are known. 100 ml of heptane, and then 19 ml (0.1 mole) of tripropylamine are introduced. The whole is heated under agitation up to back flow and then there is added drop by drop 10 ml of butanoyl chloride (0.1 mole) in solution in the heptane (50 ml).

The back flow is carried on for 60 min after the end of the addition.

Once the reactional mixture is back to room temperature, this mixture is filtered so as to eliminate the tripropylamine chlorhydrate crystals formed and the possible remnants of the di-O-isopropylidene 1,2:5,6 α-D-glucofuranose.

The filtrate collected is evaporated under reduced pressure. The product obtained (31.69 g) is a yellow pasty product with rotary power $[\alpha]_D^{22} = -28°$ (ethanol).

The V.C. analysis (OV$_{17}$; 1 m; 200° C.; 1.7 bar; retention duration 3 min) shows a purity of the order of 98%.

The totality of the product is then chromatographed on silica (Kielselgel 60, 150 g), with the assistance of an heptane/ethylic ether gradient (fraction 90/20 v/v).

The purified product (26.75 g) is in the form of a very pale yellow viscous liquid of rotary power $[\alpha]_D^{22} = -32.67°$ (ethanol), of a refractive index $n = 1.477$ at 23° C., and slightly soluble in water.

The total yield is of 81% of the product thus purified. The NMR spectrums $^1$H and $^{13}$C are given at the end of Tables 1 and 2.

EXAMPLE 2

Preparation of O-butanoyl-3-O-isopropylidene 1,2-α D-glucopyranose (II).

In this example, the mono-isopylidene derivative is prepared from the di-isopylidene derivative (compound I) prepared under the same conditions as in Example 1.

33 g (0.1 mole) of O-butanoyl-3-di-O-isopropylidene 1,2:5,6α-D-glucofuranose (butyrate -3 of glucose diacetone) are placed in an enclosure thermostated at 70° C. and containing 500 ml of $H_2SO_4$ 0.1N in a mixture of isopropanol/water (95/5 v/v).

At the end of one hour, one sees in vapour-chromatography (V.C.) the disappearance of the di-isopropylidene glucose - butyrate - 3 peak and the solution is neutralized with tripropylamine the sulfate of which is insoluble in the medium. The solvent is eliminated under a reduced pressure. The raw fraction obtained is purified by liquid chromatography on silica (Kielselgel 60 Merck 9585, 230–400 mesh, 150 g) with the assistance of a heptane/acetone gradient (fraction 80/20 v/v).

After evaporation under a reduced pressure, there is obtained 20.20 g of a slightly yellowish liquid which crystallizes F=50°-52° C. and the rotary power of which is $[\alpha]_D^{22} = +17.34°$ (chloroform).

The passage to a water/THF gradient allows the isolation of a small quantity of O-butanoyl-3-D-glucopyranose.

This quantity can be increased when one operates the hereabove hydrolysis acid at a higher temperature of 80° C. and by increasing the duration of contact (3 hours).

The derivative II which is perfectly characterized in NMR spectroscopy (Tables 1 and 2) is soluble in water at a rate of more than 100 g/l of water at room temperature.

EXAMPLE 3

Preparation of the O-butanoyl-6-O-isopropylidene-1,2α-D-glucofuranose (III).

This compound is prepared by isomerization of O-butanoyl-3O-isopropylidene 1,2α-D-glucofuranose (II) synthesized under the conditions of Example 2.

30 g of II are dissolved in 1 liter of methanol containing 10 ml of triethylamine; the mixture is stirred at room temperature for 2 hours. After evaporation under a reduced pressure, the syrup obtained, fractionated by a preparative HPLC on a WATERS column Prep. pack P/N 500-41, 75 mesh (eluant hexane-acetone, 80/20 v/v), provides:

22 g of product III, F=85-86°, $[\alpha_D^{20} = -29°$ (chloroform)

5 g of the mixture (II+III)

2 g of the starting product (II), F=50-52°, $[\alpha]_D^{20} = 17.3°$ (choroform).

The structure of the derivative III is confirmed by NMR (Tables 1 and 2).

EXAMPLE 4

Preparation of tri-O-butanoyl 3, 5, 6-O-isopropylidene-1,2 α-D-glucofuranose (IV)

This compound is prepared from O-isopropylidene-1,2-α-D-glucofuranose according to the method of Example 1 with a yield of 62% after purification on a silica gel. F=35°-36° C., $[\alpha]_D^{22} = 10.7°$ (chloroform).

The structure of the derivative IV is confirmed by NMR (Tables 1 and 2).

EXAMPLE 5

Preparation of O-n-butanoyl-6 di-O-isopropylidene-1,2:3,4α-D-galactopyranose (V).

This compound is prepared from di-O-isopropylidene-1,2:3,4α-D-galactopyranose according to the method of Example 1 with a yield of 62% after recrystallization in hexane.

F=77°-78° C.; $[\alpha]_D^{22} = 40°$ (chloroform).

The structure of the derivative 5 is confirmed by NMR (Tables 1 and 2).

EXAMPLE 6

Preparation of penta O-n-butanoyl-1,2,3,4,6 D-galactopyranose (VI).

This compound is prepared from the D-galactose according to the method of Example 1, with a yield of 83% after purification on a silica gel.

$n_D^{20} = 1.488; [\alpha]_D^{22} = +37°$ (chloroform).

The structure of derivative VI is confirmed by NMR which shows moreover the predominance of the anomer α(90%) (Tables 1 and 2).

EXAMPLE 7

Preparation of penta- O-n-butanoyl-1,2,3,4,6 D-glucopyranose (VII).

This compound is prepared from D-glucose according to the method of Example 1, with a yield of 83% after purification on a silica gel.

$n_D^{20} = 1.4516$; $[\alpha]_D^{22} = +18.3°$ (chloroform).

The structure of the derivative VII is confirmed by NMR which shows moreover the predominance of anomer α(90%) (Tables 1 and 2).

EXAMPLE 8

Preparation of O-n-butanoyl-1-isopropylidene-2,3-glyceryl (VIII)

This compound is prepared from O-isopropylidene-1,2 propanol-3 according to the method of Example 1, with a yield of 51% after purification on a silica gel. liquid, $n_D^{20} = 1.4295$.

The structure of the derivative VIII is confirmed by NMR (Tables 1 and 2).

EXAMPLE 9

Preparation of O-n-butanoyl-1, propane diol-2,3 (IX)

This compound is prepared from VIII by deprotection of the hydroxyls at 2 and 3 either in a homogeneous phase according to the method of example 2 slightly modified (6 hours at room temperature instead of 1 hour at 70° C.), or in a heterogeneous phase by passage on a column of 25 ml of Amberlist 15 Wet resin maintained at 30° C. with a flow rate of 0.1 ml/min of VIII in solution at 20% in an isopropanol-water mixture 90–10 v/v. The purification is carried out on a column of silica gel with as eluant ethyl ether.

The yields in final products are of 53% in the homogeneous phase and of 85% in the heterogeneous phase, after purification on a silica gel.

liquid, $n_D^{20} = 1.4465$.

The structure of derivative IX is confirmed by NMR (Tables 1 and 2).

EXAMPLE 10

Preparation of O-butanoyl-3-di-O-palmitoyl-1,2 glyceryl (X)

This compound is prepared from compound IX according to the method of Example 1 with a yield of 72% after purification on a silica gel.

F=54° C.

The structure of derivative X is confirmed by NMR (Tables 1 and 2).

EXAMPLE 11

Preparation of di-O-butanoyl-2,3 O-palmitoyl-1-glyceryl (XI)

This compound is prepared according to the following frequence:

a) esterification by palmitoyl chloride of the O-isopropylidene-1,2 propanol-3, according to the method of Example 1 leading to O-palmitoyl-1 O-isopropylidene-2,3 propane;

b) deprotection of the hydroxyls at 2 and 3 on the compound obtained at a) according to the methods described for the preparation of IX, producing O-palmitoyl-1 propane diol-2,3;

c) esterification by the butanoyl chloride of the compound obtained at b) according to the method of Example 1 leading to XI, with a yield of 70% after purification on a silica gel.

Liquid, $n_D^{20} = 1.4475$.

The structure of derivative XI is confirmed by NMR (Tables 1 and 2).

Pharmacologic and pharmacocinetic tests (1) TOXICITY

The toxicities which are acute with the SWISS mouse and chronic with the albino rat are determined according to the usual standardized protocols.

| COMPOUNDS | TOXICITY Median lethan dose in g/kg | |
|---|---|---|
| | i.p. route | oral route |
| I | 1.75 ± 0.39 | >8 |
| II | 4.2 ± 0.4 | >8 |
| III | 3.00 ± 0.35 | >8 |
| IV | >8 | >8 |
| V | 2.5 ± 0.4 | >8 |
| VI | >8 | >8 |
| VII | >8 | >8 |
| VIII | 5.4 ± 0.3 | >8 |
| IX | 2.25 ± 0.23 | >8 |
| X | >2 | >6 |
| XI | >8 | >8 |

The administration of 1.12 g/kg of compound I to the rat does not cause any lethality.

(2) Pharmacokinetic with the rabbit.

These tests are carried out in the following manner:

A solution containing 0.600 g of a compound according to the invention is prepared in 2 ml of glycerol formal (mixture of dioxane-1,3 ol-5 and of dioxolane - 1,3 methanol-4).

Rabbits were previously injected with (0.1 ml/kg) of a solution of heparin having a concentration of 5000 I.U./ml in the marginal vein of the ear; the needle is left in position so as to be able to administer, two minutes later, a dose of 0.1 ml/kg (that is 23 mg/kg) of the solution prepared hereabove.

Blood samplings of 1 cm³ carried out at intervals are made at the level of the marginal vein of the ear. The blood is centrifuged (2000 rev/min for 3 min) and the serum is collected.

The concentration in serum potential butyric acid is determined by gas-chromatography with the assistance of a column of CHROMOSORB 101 or of CARBOPACK C.

The sample to be analyzed by chromatography is prepared by the following treatment:

80 μl of serum

10 μl of pure formic acid

10 μl of valeric acid (internal etalon) at the concentration of 50 mg/l.

This treatment prior to chromatography has the effect of hydrolyzing the compound or its metabolites and releasing the n-butyric acid.

The quantification is made by comparing the respective surfaces of n-butyric acid and of valeric acid, the response coefficients having been determined beforehand. Thus is measured the serum concentration (in mmoles) of potential or releasable n-butyric acid from the compound or its metabolites contained in the serum. These measures allow one to determine the apparent serum half-life of the injected ester compound.

These measures afford the following results shown in Table 3.

The compounds according to the invention have a half-life time, in the blood stream of the rabbit, which is much longer than that of the saline butyrates. Thus, they form a potential reserve of butyric acid by a slow enzymatic hydrolysis with the assistance of the many esterases present in the animal or man.

(3) In vivo antitumoral tests with the mouse.

The studies on the antitumoral properties have been carried out with the mouse according the CHANY and CERRUTI protocol (Int. J. Cancer, 1982, 30, 489) on the hereabove compounds I to V.

In order to obtain a tumor or tumors with mice, one uses the TG 180 strain (injection via the i.p. route of $10^6$ cells for a male mouse of 25 g and of 0.1 ml of a solution of Corynbacterium Parvum Mérieux (CP)).

FIRST EXPERIMENT

This experiment bears on 135 SWISS mice devided into 9 batches of 15 mice each. After injection on day $D_0$ of the TG 180 and CP cells, one proceeds in the following manner:

The reference batch No. 1 is treated every day with an injection of placebo.

The reference batch No. 2 is treated every day with an injection of CP (0.1 ml).

The reference batch No. 3 is treated every day with an injection of interferon EAT-113, 0.5 ml.

The reference batch No. 4 is treated every day alternately with CP and with interferon EAT-113, with the same doses as hereabove.

The experimental batches are treated, alternately on day $D+1$ with the compound according to the invention (0.5 ml of an 8 mmolar solution of a compound I to V), on day $D+2$ with interferon EAT-113, on day $D+3$ with CP, and this for three weeks.

The number of survivors is noted, as well as the presence or not of a tumor (tumor+ or tumor−) in the survivors five weeks after day $D_0$.

The hereafter Table 4 gives the results observed.

Table 4 shows the very good antitumoral therapeutic efficiency of compounds I, II, III according to the invention, with respect to the reference batches No. 1, 2, 3 and 4.

The quantity of potential n-butyric acid which can be released in the mouse system is, in this protocol, for compounds I, II, III, of 14 mg per kilogramme of mouse, this corresponding in theory to the optimal dose advocated for the arginine butyrate for a mouse of 25 g.

SECOND EXPERIMENT

Tests according to the same protocol as hereabove for determining the dose effect of the compounds according to the invention have been carried out by maintaining constant the quantity of CP and interferon of the preceding experiment, but by varying the concentration from 0.25 to 50 millimoles of compound II per liter of injectable solution (0.5 ml of this solution being injected) that is the potential equivalent of 0.44 to 88 mg of n-butyric acid per kg of mouse, The survival after 100 days is of 1 mouse amongst 45 for the CP alone, of 0 amongst 45 for the interferon alone, of 30 amongst 45 for the compound II, whatever the concentration between 0.25 and 50 mmol/l, compound II being administered alternately with CP and interferon according to the hereabove protocol.

Another test, according to another protocol where the interferon has been omitted but where one goes on administrating alternatively 0.1 ml of CP and 0.5 ml of a solution of compound II with a concentration varying from 0.5 to 50 millimoles/l, shows that the number of surviving mice after 100 days is constant whatever the concentration of compound II and reaches an average of 20 amongst 45 mice.

These results show that a dose of compound II at most equal to the equivalent of 0.44 mg of potential n-butyric acid per kilogramme of mouse is sufficient for obtaining the maximum therapeutic effect.

This dose is about 32 times less than the optimal dose advocated for the arginine butyrate (14 mg of butyric acid) and consequently allows avoiding massive therapeutic doses with man. It should be recalled that the present necessity of a massive dose of arginine butyrate causes side effects in man, of the hyperammoniemy type with a reduction of the insulin secretion and disturbances of the urea cycle and of glucose metabolism (cf Brazier et al, Chimica Clinica Acta page 261, vol. 148, 1988).

The fact also that the association of compound II plus CP alone provides therapeutic results which are as good as the association of interferon with CP plus arginine butyrate allows considering, with the compounds according to the invention, a suppression of interferon, while the association of CP plus arginine butyrate without interferon has a low therapeutic efficiency (8 surviving mice amongst 45 after 100 days).

Other therapeutic effects have been put in evidence for the compounds according to the invention, particularly compound II. Thus:

a) compound II shows in vivo a potentialization of the action of interferon EAT-113 on the Herpes hominis type II virus;

b) the association of compound II with interferon EAT-113 has an in vitro action which is stronger than the association of arginine butyrate and interferon EAT-113 on the neoplasic mammary cells (strain NCF 410);

c) compound II has a stronger action in vitro on the cells infected by the murine AIDS TR-26 virus than the arginine butyrate;

d) the compounds according to the invention can be associated with other products, notably methotrexate, for the therapeutic treatment of tumors.

As a function of the pharmacologic results exposed hereabove, compositions are prepared for a therapeutic utilization, in man or animal, including 100 to 2000 mg of a compound according to the invention and any pharmaceutically acceptable excipient.

Thus, for example, compound II is set in an isotonic solution with a physiologic or glucosed serum in order to form an injectable drug dosed per unit between 100 and 500 mg of compound II.

Compound II is mixed possibly with an excipient such as a glycol polyethylene (GPE) for forming a drug which can be administered per oral or rectal route and dosed per unit between 1 and 2 g of compound II. For the oral administration, gastroresistant gellules are provided for avoiding acid hydrolysis in the stomach.

TABLE 1

$^1$H NMR spectrum of compounds I to VII
(BRUCKER WP.300-house reference TMS)

|  | I | II | III | IV | V | VI | VII |
|---|---|---|---|---|---|---|---|
| H-1 | 3,87 d | 5,95 d | 5,93 d | 5,88 d | 5,54 d | 6,41 d | 6,32 d |
| H-2 | 4,47 d | 4,57 d | 4,52 d | 4,41 d | 4,33 dd | 5,38 d | 5,06 dd |
| H-3 | 5,32 dd | 5,32 d | 4,33 d | 5,29 d | 4,62 dd | 5,53 d | 5,46 dd |
| H-4 | 4,21 dd | 4,20 dd | 4,16 dd | 4,42 dd | 4,24 dd | 5,38 d | 5,12 dd |
| H-5 | 4,19 q | 3,90 m | 4,03 m | 5,20 m | 4,04 m | 4,39 t | 4,07 m |
| H-6 | 4,08 m | 3,75 m | 4,36 m | 4,40 dd | 4,33 dd | 4,04 d | 4,17 dd |
| H-6' | 4,00 m |  |  | 4,10 dd | 4,16 dd |  | 4,07 dd |
| (a) |  |  |  |  |  |  |  |
| $CH_2 \alpha$ | 2,32 t | 2,40 t | 2,37 t | 2,20 m | 2,33 t | 2,12–2,57 m | 2,17–2,41 m |
| $CH_2 \beta$ | 1,67 q | 1,67 m | 1,60 m | 1,60 m | 1,66 m | 1,42–1,96 m | 1,63 m |
| $CH_3 \gamma$ | 0,95 t | 0,97 t | 0,98 t | 0,91 m | 0,96 m | 0,95 m | 0,94 m |
| (b) |  |  |  |  |  |  |  |
| $CH_3$ | 1,52 s | 1,50 | 1,45 s | 1,49 s | 1,50 s |  |  |
|  | 1,40 s | 1,32 | 1,29 s | 1,29 s | 1,45 s |  |  |
|  | 1,32 s (2×$CH_3$) |  |  |  | 1,34 s |  |  |
|  |  |  |  |  | 1,33 s |  |  |

$^1$H NMR spectrum of compounds VIII to XI
(BRUCKER WP.300-house reference TMS)

|  | VIII | IX | X | XI |
|---|---|---|---|---|
| H-1 | 4,10 dd | 4,02 d(H1+H1') | 4,25 dd | 4,31 dd |
| H-1' | 4,17 dd |  | 4,09 dd | 4,15 dd |
| H-2 | 4,32 m | 3,81 m | 5,21 m | 5,28 m |

TABLE 1-continued

| | | | | |
|---|---|---|---|---|
| H-3 | 3.74 dd | 3,56 dd | cf H-1 | cf. H-1 |
| H-3' | 4,08 dd | 3,47 dd | cf H-1' | cf. H-1' |
| $CH_2(\alpha)$ | 2,32 t | 2,22 t | 2,25 m | 2,31 m |
| $CH_2(\beta)$ | 1,65 m | 1,54 hex | 1,59 m | 1,64 m |
| $CH_3(\gamma)$ | 0,95 t | 0,84 t | 0,82–0,89 m | 0,88–0,96 m |
| | | | 1,20 s(n $CH_2$) | 1,26 s |
| (b) | | | | |
| $CH_3$ | 1,44 s | | | |
| | 1,37 s | | | |

(a) butyric rest: $O-CO-\underset{\alpha}{CH_2}-\underset{\beta}{CH_2}-\underset{\gamma}{CH_3}$ (b) isopropylidene rest

TABLE 2

$^{13}$C NMR spectrum of compounds I to VII
(BRUCKER WP.300-house reference TMS)

| | I | II | III | IV | V | VI | VII |
|---|---|---|---|---|---|---|---|
| C-1 | 105,41 | 104,72 | 104,93 | 105,20 | 96,52 | 89,93 ($\alpha$) | 88,76 ($\alpha$) |
| C-2 | 83,48 | 82,97 | 85,16 | 83,59 | 70,94 | 67,74 | 69,11 |
| C-3 | 75,95 | 76,05 | 75,33 | 74,73 | 70,70 | 67,74 | 69,96 |
| C-4 | 79,98 | 78,85 | 79,30 | 77,03 | 66,23 | 66,86 | 67,49 |
| C-5 | 72,49 | 66,22 | 68,77 | 67,63 | 71,33 | 69,27 | 69,42 |
| C-6 | 67,35 | 63,96 | 65,98 | 63,17 | 63,37 | 61,39 | 61,24 |
| (C) | 109,34 | 112,13 | 111,83 | 112,52 | 108,89 | | |
| $-O\diagdown_C\diagup CH_3$ $-O\diagup^C\diagdown CH_3$ ($CH_3$) | 112,23 25,27 26,24 26,78 26,39 | 26,01 26,40 | 26,29 26,79 | 26,31 26,81 | 109,80 24,61 25,07 26,10(2×$CH_3$) | | |
| (a) | | | | | | | |
| C=O | 172,00 | 173,32 | 174,34 | 172,18–173,15 | 173,75 | 171,51–172,71 | 171,29–173,13 |
| $C_\alpha$ | 36,13 | 35,91 | 36,03 | 35,94–36,08 | 36,19 | 35,92 | 35,58–35,58 |
| $C_\beta$ | 18,44 | 18,18 | 18,36 | 18,14–18,42 | 18,53 | 18,31–18,97 | 18,19 |
| $C_\gamma$ | 13,61 | 13,45 | 13,65 | 13,67 | 13,66 | 13,61 | 13,49 |

(a) butyric rest: $O-CO-CH_2^\alpha-CH_2^\beta-CH_3^\gamma$ ($\alpha$) anomer $\alpha$ predominant – multiplicity of signals, the chemical displacements of the various butyric chains chains not being strictly identical $^{13}$C NMR spectrum of compounds VIII to IX
(BRUCKER WP.300-house reference TMS).

| | VIII | IX | X | XI |
|---|---|---|---|---|
| C-1 | 66,38 | 63,27 | 62,13 | 61,99 |
| C-2 | 64,50 | 70,03 | 66,95 | 68,79 |
| C-3 | 73,70 | 64,83 | 62,13 | 61,99 |
| C | 109,81 | — | — | — |
| $-O\diagdown_C\diagup CH_3$ $-O\diagup\diagdown CH_3$ $CH_3$ | 25,41 26,70 | | | |
| (a) | | | | |
| C=O | 173,40 | 174,08 | 172,86 173,06 173,27 | 172,59 172,99 173,20 |
| $C_\alpha$ | 35,98 | 35,88 | 35,95 | 35,80 35,95 |
| $C_\beta$ | 18,40 | 18,19 | 18,39 | 18,26 |
| $C_\gamma$ | 13,65 | 13,48 | 13,64 | 13,49 |
| (b) | | | | |
| $C_{\alpha'}$ | — | — | 34,25 | 33,94 |
| $C_{\beta'}$ | — | — | 31,99 | 31,83 |
| 11×($CH_2$) | — | — | 24,94 29,74 | 22,59 29,58 |
| $C_{\Omega-1}$ | — | — | 22,74 | 22,59 |
| $C_\Omega$ | — | — | 14,14 | 14,01 |

(a) butyric rest: $O-CO-CH_2-CH_2-CH_3$ (b) palmitic rest: $O-CO-\underset{\alpha'}{CH_2}-\underset{\beta'}{CH_2}-(CH_2)_{11}-\underset{\Omega-1}{CH_2}-\underset{\Omega}{CH_3}$

TABLE 3

| | Compound | | | | | | | | | | |
|---|---|---|---|---|---|---|---|---|---|---|---|
| | I | II | III | IV | V | VI | VII | VIII | IX | X | XI |
| apparent serie half-life in hours | 12 | 8 | 5 | 8 | 24 | 3 | 2 | 4,33 | 2,66 | 1,75 | 3 |
| with the rabbit | | | | | | | | | | | |

TABLE 4

|  | reference batch No 1 | reference batch No 2 | reference batch No 3 | reference batch No 4 | Test batch No 5 | Test batch No 6 | Test batch No 7 | Test batch No 8 | Test batch No 9 |
| --- | --- | --- | --- | --- | --- | --- | --- | --- | --- |
| administered substances | placebo | CP | interferon | CP + interferon | compound I alternately with CP and interferon | compound II alternately with CP and interferon | III alternately with CP and interferon | IV alternately with CP and interferon | V alternately with CP and interferon |
| number of mice | 15 | 15 | 15 | 15 | 15 | 15 | 15 | 15 | 15 |
| number of animals with tumors | 15 | 15 | 15 | 14 | 9 | 10 | 7 | 13 | 12 |
| number of survivors after 6 weeks | 0 | 3 | 1 | 3 | 10 | 9 | 11 | 3* | 3* |
| number of survivors (tumor +) | 0 | 2 | 0 | 1 | 3 | 0 | 3 | 0 | 0 |
| number of survivors (tumor −) | 0 | 1 | 1 | 2 | 7 | 9 | 8 | 3 | 3 |

The small number of survivors with compounds IV and V may be explained by difficulties for solubilizing these products.

We claim:

1. A compound selected from the group consisting of O-butanoyl-3-di-O-isopropylidene-1,2:5,6α-D-glucofuranose, O-butanoyl-3-O-isopropylidene-1,2-α-D-glucofuranose, O-butanoyl-6-O-isopropylidene-1,2,αD-glucofuranose, tri-O-butanoyl 3,5,6-isopropylidene-1,2-α-D-glucofuranose, O-butanoyl-6-di-O-isopropylidene-1,2:3,4 α-D-galactopyranose and penta-O-butanoyl-1,2,3,4,6α-D-galactopyranose.

2. A composition for delivering n-butyric acid comprising an effective amount to deliver an effective amount of n-butyric acid of a compound according to claim 1 and a pharmaceutically acceptable carrier.

3. A method for administering an n-butyric glucose acid ester of a monosaccharide to a patient in need thereof whereby in vivo it releases butyric acid comprising administering to said patient an effective amount of a compound selected from the group consisting of O-butanoyl-3-di-O-isopropylidene-1,2:5,6-α-D-glucofuranose, O-butanoyl-3-O-isopropylidene-1,2-α-D-glucofuranose, O-butanoyl-6-O-isopropylidene-1,2,αD-glucofuranose, tri-O-butanoyl-3, 5, 6-isopropylidene-1,2 α-D-glucofuranose, O-butanoyl-6-di-O-isopropylidene-1,2:3,4 α-D-galactopyranose, and penta-O-butanoyl-1,2,3,4,6α D-galactopyranose, whereby said ester in vivo releases n-butyric acid.

4. The method according to claim 3 wherein the compound is O-butanoyl-3-O-isopropylidene 1,2-α D-glucopyranose.

* * * * *